United States Patent [19]

Clarkson et al.

[11] Patent Number: 5,668,009
[45] Date of Patent: Sep. 16, 1997

[54] METHODS FOR TREATING COTTON-CONTAINING FABRICS WITH CBH I ENRICHED CELLULASE

[75] Inventors: Kathleen A. Clarkson, San Francisco; Kathy Collier, Hillsborough; Pushkaraj J. Lad, San Mateo; Geoffrey L. Weiss, San Francisco, all of Calif.

[73] Assignee: Genencor International, Inc., Palo Alto, Calif.

[21] Appl. No.: 401,126

[22] Filed: Mar. 9, 1995

Related U.S. Application Data

[63] Continuation of Ser. No. 236,144, May 2, 1994, abandoned, which is a continuation of Ser. No. 878,950, May 1, 1992, abandoned.

[51] Int. Cl.$^6$ .................................................. D06M 16/00
[52] U.S. Cl. ........................ 435/263; 435/264; 435/209; 435/945; 8/101; 510/320
[58] Field of Search ................................... 435/263, 264, 435/209, 401, 945; 252/174.12, DIG. 12; 8/116.1, 101

[56] References Cited

U.S. PATENT DOCUMENTS

| | | | |
|---|---|---|---|
| 3,844,890 | 10/1974 | Horikoshi et al. | 195/62 |
| 4,275,163 | 6/1981 | Gallo | 435/209 |
| 4,435,307 | 3/1984 | Barbesgaard et al. | 252/174 |
| 4,443,355 | 4/1984 | Murata et al. | 252/174 |
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,648,979 | 3/1987 | Parslow et al. | 252/8.8 |
| 4,661,289 | 4/1987 | Parslow et al. | 252/547 |
| 4,725,544 | 2/1988 | Tan et al. | 435/200 |
| 4,738,682 | 4/1988 | Boegh et al. | 8/401 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174 |
| 4,832,864 | 5/1989 | Olson | 252/174.12 |
| 4,894,338 | 1/1990 | Knowles et al. | 435/172 |
| 4,912,056 | 3/1990 | Olson | 435/263 |
| 4,945,053 | 7/1990 | Ito et al. | 435/209 |
| 4,952,505 | 8/1990 | Cho | 435/209 |
| 4,978,470 | 12/1990 | Suzuki et al. | 252/174 |
| 5,006,126 | 4/1991 | Olson et al. | 8/401 |
| 5,045,464 | 9/1991 | Ito et al. | 435/209 |
| 5,120,463 | 6/1992 | Bjork et al. | 435/264 |
| 5,246,853 | 9/1993 | Clarkson et al. | 435/263 |
| 5,290,474 | 3/1994 | Clarkson et al. | 252/174.12 |
| 5,419,778 | 5/1995 | Clarkson et al. | 8/116.1 |

FOREIGN PATENT DOCUMENTS

| | | |
|---|---|---|
| 0120528 | 10/1984 | European Pat. Off. |
| 0137280 | 4/1985 | European Pat. Off. |
| 0173397 | 3/1986 | European Pat. Off. |
| 0220016 | 4/1987 | European Pat. Off. |
| 0244234 | 4/1987 | European Pat. Off. |
| 0271004 | 12/1987 | European Pat. Off. |
| 0 268 169 | 6/1988 | European Pat. Off. |
| 0 270 974 | 6/1988 | European Pat. Off. |
| 0 273 125 | 7/1988 | European Pat. Off. |
| 0 269 168 | 6/1989 | European Pat. Off. |
| 32 07825 A1 | 9/1982 | Germany |
| 2148278 | 9/1984 | Germany |
| 58-54082 | 3/1982 | Japan |
| 58-36217 | 3/1983 | Japan |
| 62-62898 | 3/1987 | Japan |
| 64-40681 | 2/1989 | Japan |
| 2095275 | 3/1972 | United Kingdom |
| 1368599 | 10/1974 | United Kingdom |
| 2094826 | 9/1982 | United Kingdom |
| 85/04672 | 6/1985 | WIPO |
| 89/09259 | 10/1985 | WIPO |
| 91/05841 | 5/1991 | WIPO |
| 9206183 | 4/1992 | WIPO |

OTHER PUBLICATIONS

S. Aho, "Structural and functional analysis of *Trichoderma reesei* endoglucanase I expressed in yeast *Saccharomyces cerevisiae*", *FEBS Letters*, vol. 291, No. 1, pp. 45–49 (1991).

Berg et al., "Enzyme–Gold Affinity Labelling of Cellulose", *Journal of Electron Microsc. Tech.*, vol. 8, No. 4, pp. 371–379, (1988) [Abstract].

Bhat et al., "The Endo–(1–4)–β–D–Glucanase System of *Penicillin Pinophilam* Cellulase: Isolation, Purification and Characterization of 5 Major Endoglucanase Components", *Carbohydrate Research*, vol. 190, pp. 279–297 (1989).

Brown et al., "Microbial Enzymes and Lignocellulose Utilization," *Genetic Control of Environmental Pollutants*, Omen et al. (Editor), Plenum Publishing Corp., pp. 239–265 (1984).

Chen et al., "Nucleotide Sequence and Deduced Primary Structure of Cellobiohydrolase II from *Trichoderma reesei*", *Biotechnology*, vol. 5, pp. 274–278 (1987).

Hakansson et al., "Purification and Characterization of a Low Molecular Weight 1,4–β–Glucan Glucanohydrolase from the Cellulolytic Fungus *Trichoderma Ciride*, QM9414", *Biochimica et Biophysica Acta* vol. 524, 385–392 (1978).

Hakanssan, Dissertation, Faculty of Science, Uppsala University, pp. 6–23 (1981).

(List continued on next page.)

*Primary Examiner*—Carolyn Paden
*Attorney, Agent, or Firm*—Christopher L. Stone

[57] ABSTRACT

Disclosed are improved methods for treating cotton-containing fabrics as well as the fabrics produced from these methods. In particular, the disclosed methods are directed to contacting cotton-containing fabrics with an aqueous solution containing a fungal cellulase composition which comprises CBH I type components and one or more EG type components wherein said cellulase composition has a protein weight ratio of CBH I type components to all EG type components of greater than 10:1. Cotton-containing fabrics so treated possess decreased strength loss as compared to fabrics treated with a complete cellulase composition.

11 Claims, 6 Drawing Sheets

OTHER PUBLICATIONS

Harkki et al., "Genetic engineering of *Trichoderma* to produce strains with novel cellulase profiles", *Enzyme Microb. Technol.*, vol. 13, pp. 227–233 (1991).

Hayashida et al., "Cellulases of *Humicola insolens* and *Humicola grisea*", *Methods in Enzymology*, vol. 160, pp.323–332 (1988).

Hayashida et al., "Production and Purification of Thermostable Cellulases from *Humicola insolens* YH–8", *Agri. Biol. Chem.*, vol. 44(8), pp. 1721–1728 (1980).

Hayashida et al., "The Role of Carbohydrate Moiety on Thermostability of Cellulases from *Humicola insolens* YH–8", *Agri. Biol. Chem.*, vol. 44(3) pp. 481–487 (1980). *International Textile Bulletin, Dyeing/Printing/Finishing*, 2nd Quarter, pp. 5–8 (1990).

"Weight Loss Treatment to Soften the Touch of Cotton Fabric", *JTN*, p. 64 (Dec. 1988).

Knowles et al., "The use of gene technology in the development of novel cellulolytic organisms–*Trichoderma reesei* cellulase and cellulobiohydrolase gene cloning and expression; a review", *Recent Adv. Biotechnol. Appl. Biol.*, pp. 139–142 (1988) [Abstract].

Knowles et al., "The use of gene technology to investigate fungal cellulolytic enzymes *Trichoderma reesei* cellulase complex gene cloning and expression in *Saccharomyces cerevisiae*", *FEMS Symp.* 43, pp. 153–169 (1988) [Abstract].

Kubicek–Pranz et al., "Transformation of *Trichoderma reesei* with cellobiohydrolase II gene as a means for obtaining strains with increased cellulase production and specific activity", *Journal of Biotechnology*, vol. 20, pp. 83–94 (1991).

Kubicek–Pranz et al., "Characterization of Commercial *Trichoderma–reesei* Cellulase Preparations by Denaturing Electrophoresis SDS–PAGE and Immunostaining Using Monoclonal Antibodies", *Biotechnol. Appl. Biochem.*, vol. 14, pp. 317–323 (1991) [Abstract].

Luderer et al., "A Re–appraisal of Multiplicity of Endoglucanase I from *Trichoderma reesei* Using Monoclonal Antibodies and Plasma Desorption Mass Spectrometry", *Biochim. Biophys. Acta*, vol. 1076, No. 3, pp. 427–434 (1991) [Abstract].

Miller et al., "Direct and Indirect Gene Replacements in *Aspergiillus nidulans*," *Mol. and Cell. Biol.*, vol. 5(7), pp. 1714–1721 (1985).

Murphy–Holland et al., "Secretion activity and stability of deglycosylated cellulase of *Trichoderma reesei* gene cloning", *Abstr. Annu. Meet. Am. Soc. Microbiol.*, 85 Meet., 193 (1985) [Abstract].

Ohishi et al., "Reformation of Cotton Fabric by Cellulase", pp. 1–12 (Mar. 1987) [Translation and Original].

Penttilla et al., "Homology between cellulase genes of *Trichoderma reesei*: complete nucleotide sequence of the endoglucanase I gene", *Gene*, vol. 45, pp. 253–263 (1986).

Penttillä et al., "Expression of Two *Trichoderma reesei* Endoglucanases in the Yeast *Saccharomyces cerevisiae*", *Yeast*, vol. 3, pp. 175–185 (1987).

Reinikainen et al., "How Do *Trichoderma reesei* cellobiohydrolase bind to and degrade cellulose", *Abstr. Pap. Am. Chem. Soc.*, 202 Meet. Pt. 1 (1991) [Abstract].

Saloheimo et al., "EGIII a new endoglucanase from *Trichoderma reesei*: the characterization of both gene and enzyme", *Gene*, vol. 63, pp. 11–21 (1988).

Sambrook et al., *Molecular Cloning A Laboratory Manual*, 2nd Ed., Cold Spring Harbor Laboratory Press, pp. 1.53–1.73 (1989).

Schulein, "Cellulases of *Trichoderma reesei*", *Methods in Enzymology*, vol. 160, pp. 234–242 (1988).

Sheir–Neiss etal., "Characterization of the Secreted Cellulases of *Trichoderma reesei* Wild Type and Mutants During Controlled Permentations", *Appl. Microbiol. Biotechnol.*, vol. 20, pp. 46–53 (1984).

Shoemaker et al., "Molecular Cloning of Exo–cellobiohydrolase I Derived from *Trichoderma reesei* Strain L27", *Biotechnology*, vol. I, pp. 691–695 (1983).

Shoemaker et al., "Characterization and Properties of Cellulases Purified from *Trichoderma reesei* Strain L27", *Biotechnology*, pp. 687–690 (1983).

Teeri, "The Cellulolytic Enzyme System of Trichoderma reesei," *Publications* 38, pp. 13, 17–20 of 1–52+Appendices (1987).

Teeri et al., "Engineering *Trichoderma* and its cellulases *Trichoderma reesei* cellulase and cellobiohydrolase gene cloning and expression: potential strain and improvement and enzyme engineering" *Trichoderma reesei Cellulases.*, pp. 156–163 (1990) [abstract].

Ulker et al., "Characterization of an Unglycosylated Low Molecular Weight 1,4–β–glucanglucanahydrolose of *Trichoderma reesei*", *FEMS Microbiology Letters*, vol. 69, pp. 215–220 (1990).

Uusitalo et al., "Enzyme Production by recombinant *Trichoderma reesei* strains" *Journal of Biotechnology*, vol. 17, pp. 35–50 (1991).

Voragen et al., "Cellulases of a Mutant Strain of *Trichodema Uride* QM 9414", *Methods in Enzymology*, vol. 160, pp. 243–251 (1988).

Wood "Properties of Cellulolytic Enzyme Systems", *Biochem. Soc. Trans.*, vol. 13, pp. 407–410 (1985).

Wood et al., "Aerobic and Anaerobic Fungal Cellulases, With Special Reference to Their Mode of Attack on Crystalline Cellulose", *Biochemistry and Genetics of Cellulose Degradation*, pp. 31–52 (1988).

Wood et al., "Methods for Measuring Cellulase Activities", *Methods in Enzymology*, vol. 160, pp. 87–112 (1988).

Wood et al., "The Mechanism of Fungal Cellulase Action", *Biochem. J.*, vol. 260, pp. 37–43 (1989).

Yamagishi, "Reforming of Cellulosic Fiber With Cellulase", *The Shizuoka Prefectural Hamamatsu Textile Industrial Research Institute Report*, vol. 24, pp. 54–61 (1986).

Chanzy et al., "The Action of 1,4–β–D–Glucan Cellobiohydrolase on *Valonia* Cellulose Microcrystals", *FEBS Letters*, vol. 153, No. 1, pp. 113–118 (Mar. 1983).

Fagerstam et al., "The 1,4–β–Glucan Celliobiohydrolases of *Trichoderma Reesei* QM 9414", *FEBS Letters*, vol. 119, No. 1, pp. 97–100 (Sep. 1980).

Henrissat et al., "Cellulase Families Revealed by Hydrophobic Cluster Analysis", *Gene*, vol. 81, pp. 83–95 (1989).

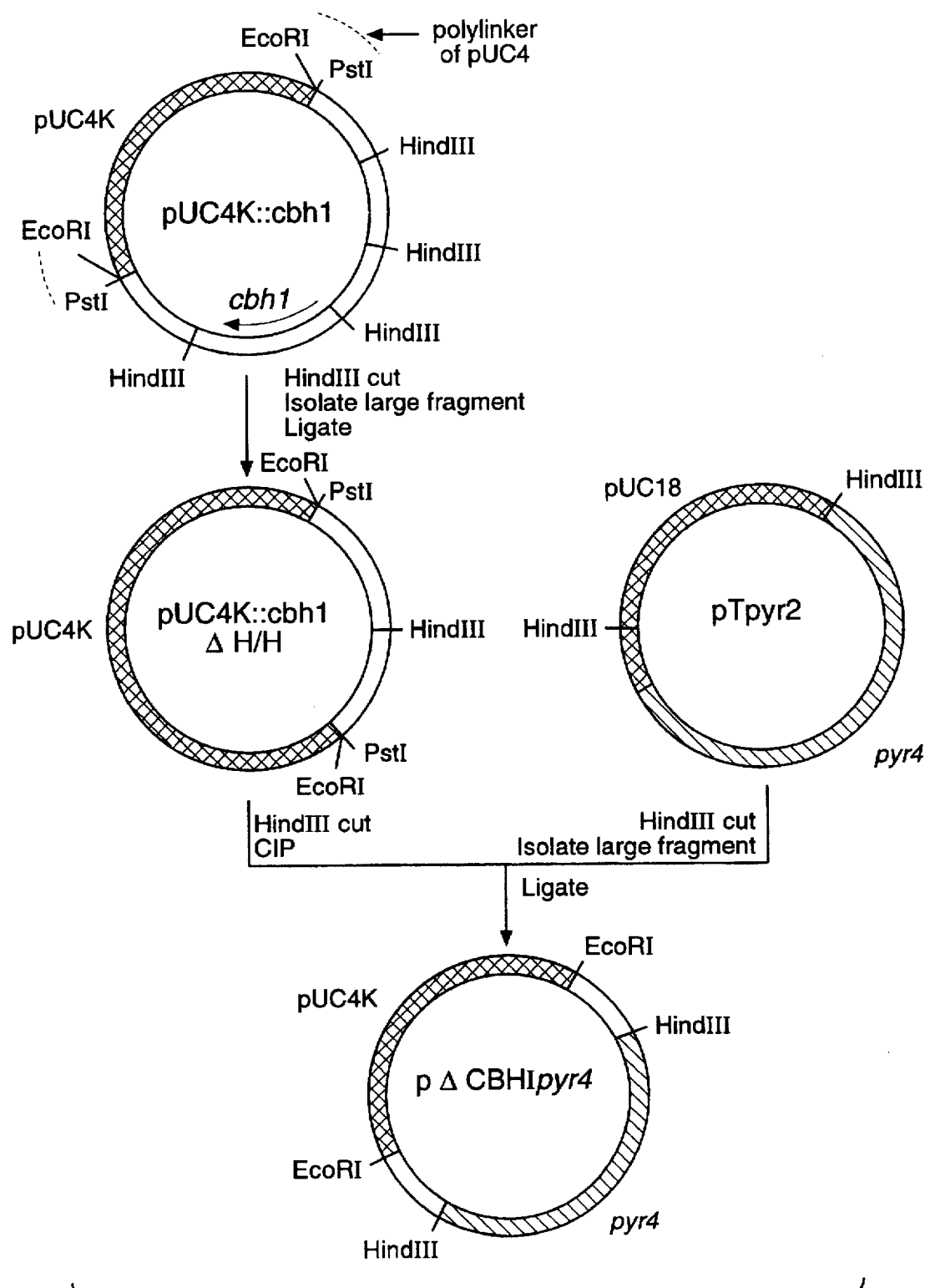
FIG._1

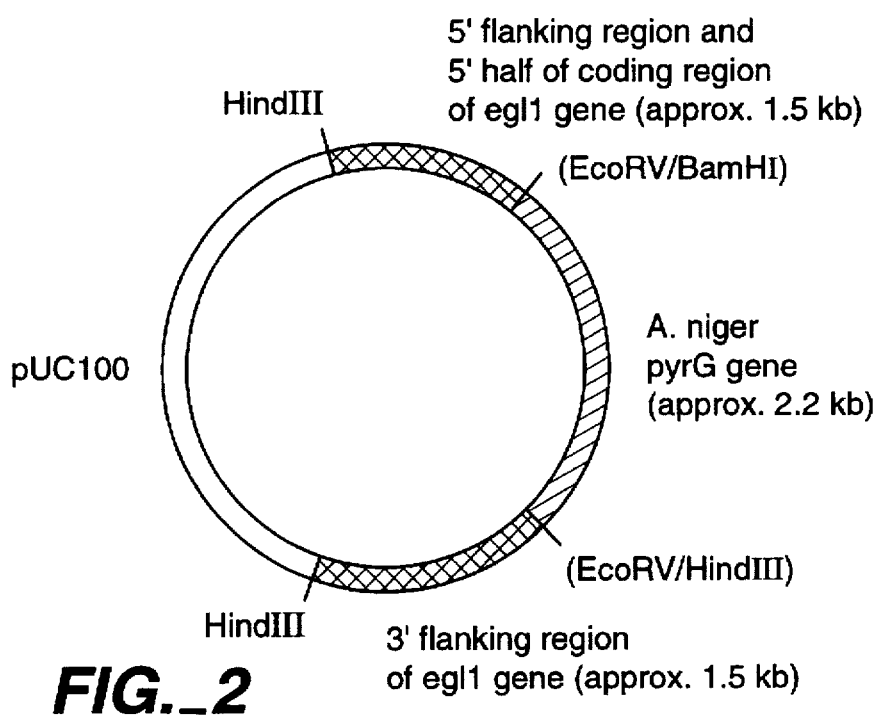
FIG._2
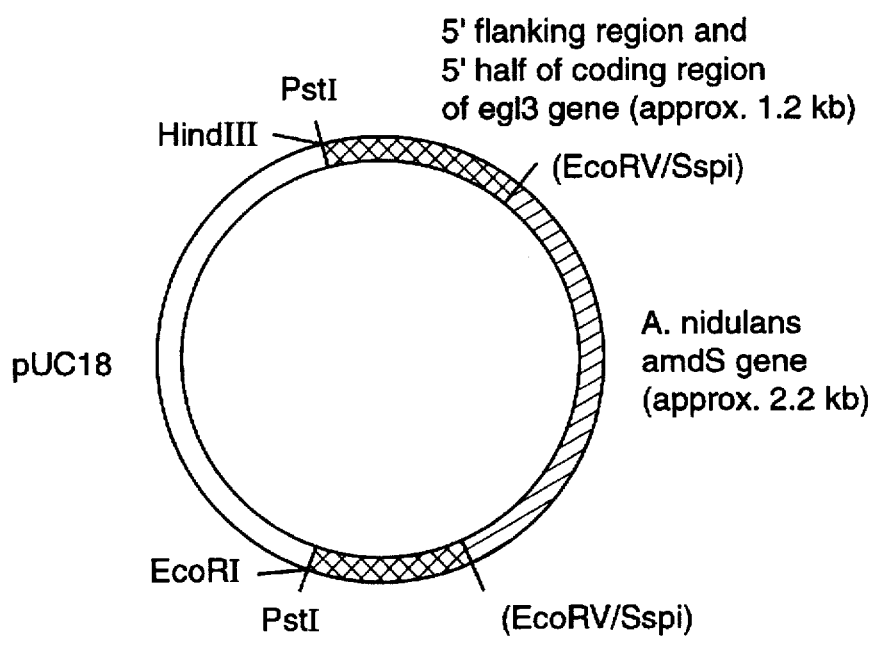
FIG._4

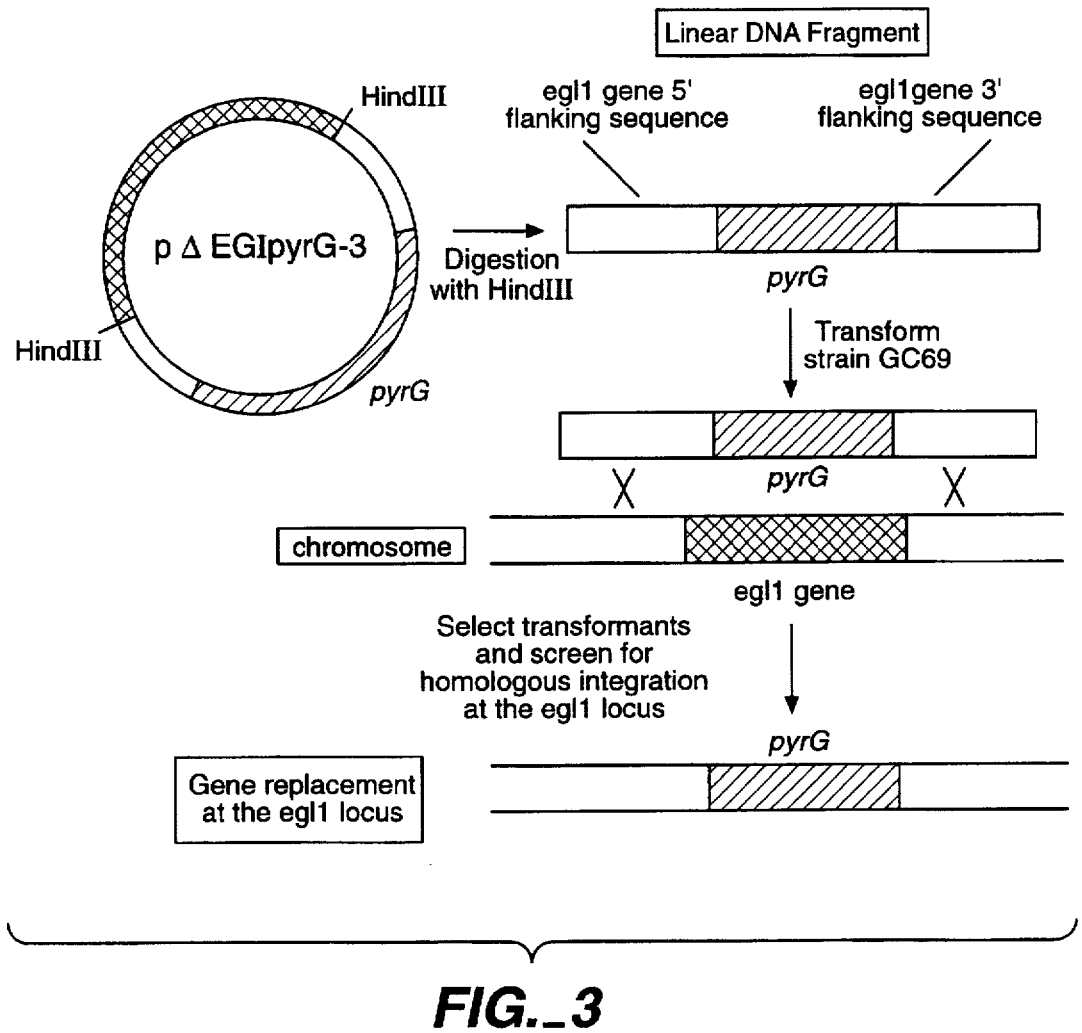
FIG._3

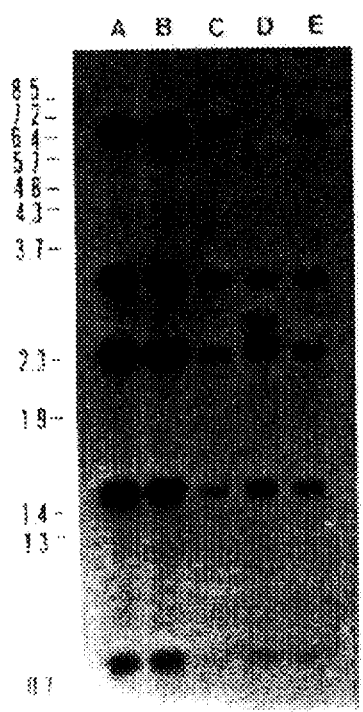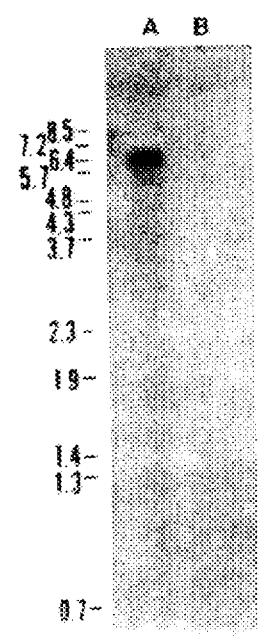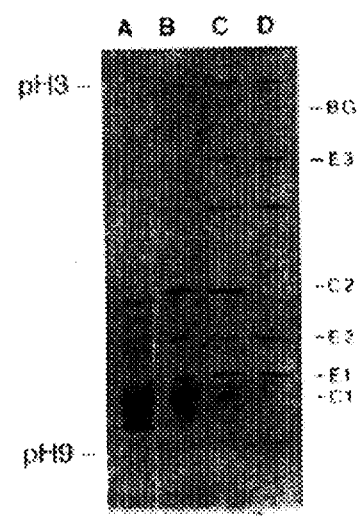
FIG._5   FIG._7   FIG._8

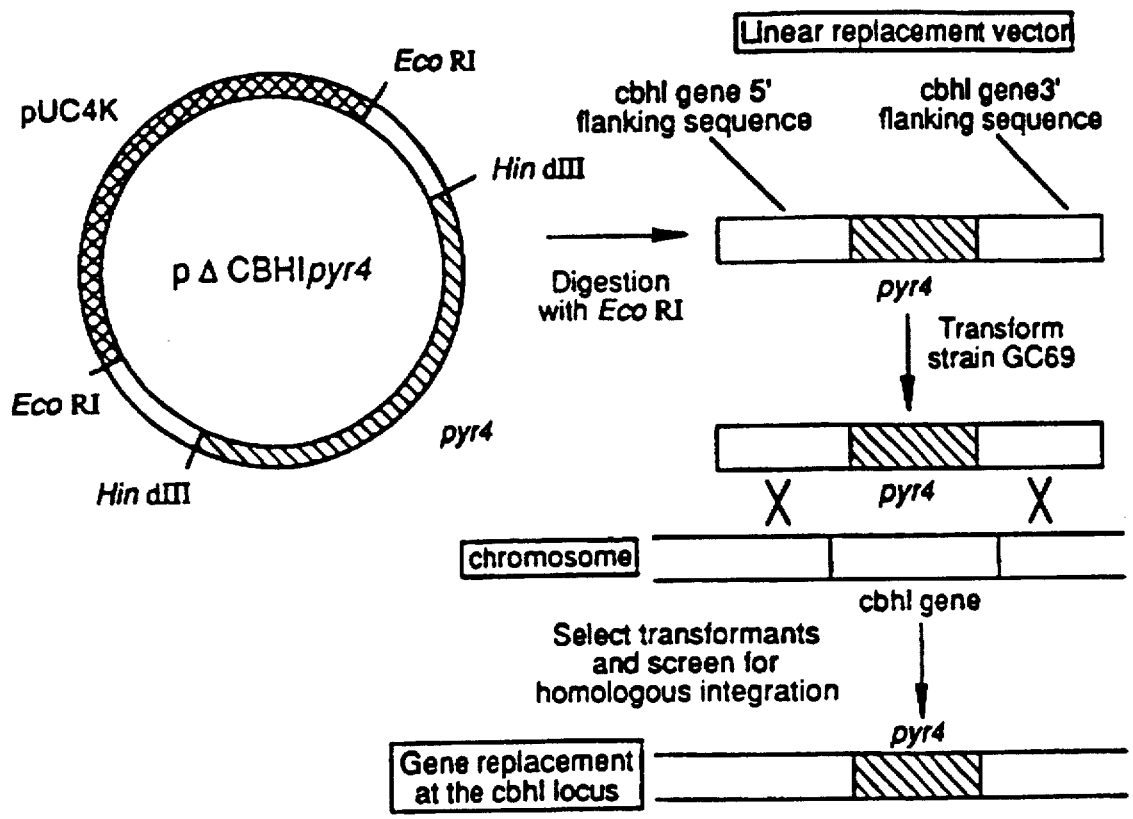
FIG. _6

METHODS FOR TREATING COTTON-CONTAINING FABRICS WITH CBH I ENRICHED CELLULASE

This application is a continuation of application Ser. No. 08/236,144, filed May 2, 1994, now abandoned which in turn is a continuation of application Ser. No. 08/878,950, filed May 1, 1992, now abandoned.

BACKGROUND OF THE INVENTION

1. Field of the Invention

The present invention is directed to improved methods for treating cotton-containing fabrics with cellulase as well as to the fabrics produced from these methods. In particular, the improved methods of the present invention are directed to contacting cotton-containing fabrics with an aqueous solution containing a fungal cellulase composition which comprises a combination of exo-cellobiohydrolase I type components and endoglucanase components wherein the exo-cellobiohydrolase I type components are enriched relative to the endoglucanase type components. When the cotton-containing fabric is treated with such solutions, the resulting fabric possesses the expected enhancements in, for example, feel, appearance, and/or softening, etc., as compared to the fabric prior to treatment and the fabric also possesses reduced strength loss as compared to the fabric treated with a complete cellulase composition.

2. State of the Art

During or shortly after their manufacture, cotton-containing fabrics can be treated with cellulase in order to impart desirable properties to the fabric. For example, in the textile industry, cellulase has been used to improve the feel and/or appearance of cotton-containing fabrics, to remove surface fibers from cotton-containing knits, for imparting a stone washed appearance to cotton-containing denims and the like.

In particular, Japanese Patent Application Nos. 58-36217 and 58-54082, as well as Ohishi et al., "Reformation of Cotton Fabric by Cellulase", and *JTN* December 1988 journal article "What's New—Weight Loss Treatment to Soften the Touch of Cotton Fabric" each disclose that treatment of cotton-containing fabrics with cellulase results in an improved feel for the fabric. It is generally believed that this cellulase treatment removes cotton fuzzing and/or surface fibers which reduces the weight of the fabric. The combination of these effects imparts improved feel to the fabric, i.e., the fabric feels more like silk.

Additionally, it was heretofore known in the art to treat cotton-containing knitted fabrics with a cellulase solution under agitation and cascading conditions, for example, by use of a jet, for the purpose of removing broken fibers and threads common to these knitted fabrics. When so treated, buffers are generally not employed because they are believed to adversely affect dye shading with selected dyes.

It was still further heretofore known in the art to treat cotton-containing woven fabrics with a cellulase solution under agitation and cascading conditions. When so treated, the cotton-containing woven fabric possesses improved feel and appearance as compared to the fabric prior to treatment.

Lastly, it was also heretofore known that the treatment of cotton-containing dyed denim with cellulase solutions under agitating and cascading conditions, i.e., in a rotary drum washing machine, would impart a "stone washed" appearance to the denim.

A common problem associated with the treatment of such cotton-containing fabrics with a cellulase solution is that the treated fabrics exhibit significant strength loss as compared to the untreated fabric. Strength loss arises because the cellulase hydrolyzes cellulose ($\beta$-1,4-glucan linkages) which, in turn, can result in a breakdown of a portion of the cotton polymer. As more and more cotton polymers are disrupted (broken down), the tensile strength of the fabric is reduced.

Because methods involving agitation and cascading of cellulase solutions over cotton woven fabrics require shorter reaction times, these methods are believed to provide cotton-containing woven fabrics of reduced strength loss as compared to cellulase treatment methods not involving agitation and cascading. In any event, such methods still nevertheless result in significant strength loss.

Accordingly, it would be particularly desirable to modify such cellulase treatment methods so as to provide reduced strength loss while still achieving the desired enhancements in the treated cotton-containing fabric arising from treatment with cellulase as compared to the fabric prior to treatment.

Additionally, because fungal sources of cellulase are known to secrete very large quantities of cellulase and further because fermentation procedures for such fungal sources as well as isolation and purification procedures for isolating the cellulase are well known in the art, it would be particularly advantageous to use such fungal cellulases in the methods for improving feel and/or appearance.

SUMMARY OF THE INVENTION

The present invention is directed to the discovery that heretofore known methods for treating cotton-containing fabrics with fungal cellulases can be improved by employing a fungal cellulase composition enriched in CBH I type cellulase components relative to EG components. Surprisingly, it has been found that a cellulase composition which contains a weight ratio of CBH I type components to EG type components of greater than about 10:1 is capable of imparting enhancements to the treated fabric with regard to feel, appearance and softness, color enhancement, and/or a stone washed appearance as compared to fabric before treatment with such a cellulase composition. Accordingly, in the present invention, the cellulase composition employed to treat cotton-containing fabrics is tailored so as to contain sufficiently high concentrations of CBH I type components so as to be strength loss resistant.

In view of the above, in one of its method aspects, the present invention is directed to an improved method for the treatment of cotton-containing fabrics with a fungal cellulase composition wherein said improvement comprises employing a fungal cellulase composition which comprises CBH I type cellulase components and EG type cellulase components wherein the protein weight ratio of CBH I type components to EG type components is greater than about 10:1.

In a preferred embodiment, the cellulase composition employed herein comprises CBH I type components and one or more EG type components wherein said cellulase composition has a protein weight ratio of CBH I type components to all EG type components of greater than 20:1.

In another of its method aspects, the present invention is directed to an improved method for the treatment of cotton-containing fabrics with an aqueous fungal cellulase solution wherein said method is conducted with agitation of the cellulase solution under conditions so as to produce a cascading effect of the cellulase solution over the fabric wherein said improvement comprises employing a fungal cellulase composition which comprises CBH I type components and one or more EG type components wherein said cellulase composition has a protein weight ratio of all CBH I type components to all EG type components of greater than 10:1. In a preferred embodiment, the fungal cellulase composition employed herein comprises CBH I type components and one or more EG type components wherein said cellulase composition has a protein weight ratio of CBH I type components to all EG type components of greater than 20:1.

Cotton-containing fabrics treated by the methods of this invention have the expected enhancement(s) as compared to the fabric prior to treatment while exhibiting reduced strength loss as compared to the fabric treated with a complete cellulase composition. The reduced strength loss evidences that the methods of this invention are strength loss resistant.

In its composition aspects, the present invention is directed to a cotton-containing fabric treated in the methods of this invention as defined above.

BRIEF DESCRIPTION OF THE DRAWINGS

FIG. 1 is an outline of the construction of pΔCBHIpyr4.

FIG. 2 is an outline of the construction of pΔEGIpyrG-3.

FIG. 3 illustrates deletion of the egl1 gene by integration of the HindIII fragment from pΔEGIpyrG-3 at the egl1 locus on one of the *T. longibrachiatum* chromosomes.

FIG. 4 is an outline of the construction of pAΔEGII-1.

FIG. 5 is an autoradiograph of DNA from *T. longibrachiatum* strain GC69 transformed with EcoRI digested pΔCBHIpyr4 after Southern blot analysis using a $^{32}P$ labelled pΔCBHIpyr4 as the probe. The sizes of molecular weight markers are shown in kilobase pairs to the left of the Figure.

FIG. 6 illustrates deletion of the *T. longibrachiatum* gene by integration of the larger EcoRI fragment from pΔCBHIpyr4 at the cbh1 locus on one of the *T. longibrachiatum* chromosomes.

FIG. 7 is an autoradiograph of DNA from a *T. longibrachiatum* strain GC69 transformed with EcoRI digested pΔCBHIpyr4 using a $^{32}P$ labelled pIntCBHI as the probe. The sizes of molecular weight markers are shown in kilobase pairs to the left of the Figure.

FIG. 8 is an isoelectric focusing gel displaying the proteins secreted by the wild type and by transformed strains of *T. longibrachiatum*. Specifically, in FIG. 8, Lane A of the isoelectric focusing gel employs partially purified CBHI from *T. longibrachiatum*; Lane B employs a wild type *T. longibrachiatum*; Lane C employs protein from a *T. longibrachiatum* strain with the cbh1 gene deleted; and Lane D employs protein from a *T. longibrachiatum* strain with the cbh1 and cbh2 genes deleted. In FIG. 8, the right hand side of the figure is marked to indicate the location of the single proteins found in one or more of the secreted proteins. Specifically, BG refers to the β-glucosidase, E1 refers to endoglucanase I, E2 refers to endoglucanase II, E3 refers to endoglucanase III, C1 refers to exo-cellobiohydrolase I and C2 refers to exo-cellobiohydrolase II.

DETAILED DESCRIPTION OF THE PREFERRED EMBODIMENTS

Figure 9A:
FIG. 9A is a representation of the *T. longibrachiatum* cbh2 locus, cloned as a 4.1 kb EcoRI fragment on genomic DNA

As noted above, the methods of this invention are improvements in prior art methods for treating cotton-containing fabrics with cellulase. The improvement comprises using a specific cellulase composition which imparts the desired enhancement(s) to the fabric while minimizing strength loss in the fabric. However, prior to discussing this invention in detail, the following terms will first be defined.

1. Definitions

The term "cotton-containing fabric" refers to sewn or unsewn fabrics made of pure cotton or cotton blends including cotton woven fabrics, cotton knits, cotton denims, cotton yarns and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. It is contemplated that regenerated cellulose, such as rayon, could be used as a substitute for cotton in the methods of this invention.

The term "finishing" as employed herein means the application of a sufficient amount of finish to a cotton-containing fabric so as to substantially prevent cellulolytic activity of the cellulase on the fabric. Finishes are generally applied at or near the end of the manufacturing process of the fabric for the purpose of enhancing the properties of the fabric, for example, softness, drapability, etc., which additionally protects the fabric from reaction with cellulases. Finishes useful for finishing a cotton-containing fabric are well known in the art and include resinous materials, such as melamine, glyoxal, or ureaformaldehyde, as well as waxes, silicons, fluorochemicals and quaternaries. When so finished, the cotton-containing fabric is substantially less reactive to cellulase.

The term "cellulase" or "cellulase composition" refers to the enzyme composition derived from fungal sources or microorganisms genetically modified so as to incorporate and express all or part of the cellulase genes obtained from a fungal source (sometimes referred to a "fungal cellulase composition"). Cellulases act on cellulose and its derivatives to hydrolyze cellulose and give primary products, glucose and cellobiose. Fungal cellulases are distinguished from cellulases produced from non-fungal sources including microorganisms such as actinomycetes, gliding bacteria (myxobacteria) and true bacteria. Fungi capable of producing cellulases useful in preparing cellulase compositions described herein are disclosed in British Patent No. 2 094 826A, the disclosure of which is incorporated herein by reference.

Most cellulases generally have their optimum activity in the acidic or neutral pH range although some fungal cellulases are known to possess significant activity under neutral and slightly alkaline conditions, i.e., for example, cellulase derived from *Humicola insolens* is known to have activity in neutral to slightly alkaline conditions.

Cellulases are known to be comprised of several enzyme classifications having different substrate specificity, enzymatic action patterns, and the like. Additionally, enzyme components within each classification can exhibit different molecular weights, different degrees of glycosylation, different isoelectric points, different substrate specificity etc.

For example, cellulases can contain cellulase classifications which include endoglucanases (EGs), exo-cellobiohydrolases (CBHs), β-glucosidases (BGs), etc. On the other hand, while bacterial cellulases are reported in the literature as containing little or no CBH components, there are a few cases where CBH-like components derived from bacterial cellulases have been reported to possess exo-cellobiohydrolase activity.

A cellulase composition produced by a naturally occurring fungal source and which comprises one or more CBH and EG components wherein each of these components is found at the ratio produced by the fungal source is sometimes referred to herein as a "complete cellulase system" or a "complete cellulase composition" to distinguish it from the classifications and components of cellulase isolated therefrom, from incomplete cellulase compositions produced by bacteria and some fungi, or from a cellulase composition obtained from a microorganism genetically modified so as to overproduce, underproduce, or not produce one or more of the CBH and/or EG components of cellulase.

The fermentation procedures for culturing fungi for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

"Endoglucanase ("EG") type components" refer to all of those cellulase components or combination of components which exhibit textile activity properties similar to the endoglucanase components of *Trichoderma longibrachiatum*. In this regard, the endoglucanase components of *Trichoderma longibrachiatum* (specifically, EG I, EG II, EG III, and the like either alone or in combination) impart improved feel, improved appearance, softening, color enhancement, and/or a stone washed appearance to cotton-containing fabrics (as compared to the fabric prior to treatment) when these components are incorporated into a textile treatment medium and the fabric is treated with this medium. Accordingly, endoglucanase type components are those fungal cellulase components which impart improved feel, improved appearance, softening, color enhancement, and/or a stone washed appearance to cotton-containing fabrics (as compared to the fabric before treatment) when these components are incorporated into a medium used to treat the fabrics and which impart reduced strength loss to cotton-containing fabrics as compared to the strength loss arising from treatment with a complete cellulase system derived from *Trichoderma longibrachiatum*.

Such endoglucanase type components may not include components traditionally classified as endoglucanases using traditional biochemical activity tests. For example, such traditional activity tests are based on the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid swollen cellulose (e.g., Walseth cellulose) and hydrolyze less readily the more highly crystalline forms of cellulose (e.g., Avicel, Solkafloc, etc.). In contrast, it is believed that not all endoglucanase components, as defined by such activity tests, will provide improved softness, feel and color retention/restoration. Accordingly, it is more accurate for the purposes herein to define endoglucanase type components as those components of fungal cellulase which possess similar textile activity properties as possessed by the endoglucanase components of *Trichoderma longibrachiatum*.

Cellulases can contain more than one EG type component. The different components generally have different isoelectric points, different molecular weights, different degrees of glycosylation, different substrate specificity, different enzymatic action patterns, etc. The different isoelectric points of the components allow for their separation via ion exchange chromatography and the like. In fact, the isolation of components from different fungal sources is known in the art, an example of which is provided in Example 1 hereinbelow. See, for example, Schulein et al., International Application WO 89/09259, Wood et al., *Biochemistry and Genetics of Cellulose Degradation*, pp. 31 to 52 (1988); Wood et al., *Carbohydrate Research*, Vol. 190, pp. 279 to 297 (1989); Schulein, *Methods in Enzymology*, Vol. 160, pp. 234 to 242 (1988); and the like. The entire disclosure of each of these references is incorporated herein by reference.

In general, it is contemplated that combinations of EG type components may give a synergistic response in improving softening, color retention/restoration and feel as compared to a singly EG type component. On the other hand, a single EG type component may be more stable or have a broader spectrum of activity over a range of pHs. Accordingly, the EG type components employed in this invention can be either a single EG type component or a combination of two or more EG type components. When a combination of components is employed, the EG type component may be derived from the same or different fungal sources.

It is contemplated that EG type components can also be derived from bacterially derived cellulases.

"Exo-cellobiohydrolase type ("CBH type") components" refer to those fungal cellulase components which exhibit textile activity properties similar to CBH I and/or CBH II cellulase components of *Trichoderma longibrachiatum*. In this regard, when used in the absence of EG type cellulase components (as defined above), the CBH I and CBH II components of *Trichoderma longibrachiatum* alone do not impart any significant enhancements in feel, appearance, color enhancement and/or stone washed appearance to the so treated cotton-containing fabrics. As the concentration of EG type components approaches that of whole cellulase, which has a ratio of about 2.5:1, enhanced strength loss occurs to the cotton-containing fabrics, as compared to cellulase compositions containing a ratio of CBH I type to EG type components of greater than 5:1. CBH refers to those components which exhibit exo-cellobiohydrolase activity; that is to say that such components degrade cellulose by hydrolyzing cellobiose from the non-reducing end of the cellulose polymer chains. CBH exhibits multiplicity and there are two CBHs from *T. reesei*, CBH I and CBH II. CBH I type cellulase components exhibit a strong binding affinity for cellulose fibers with no apparent preference for the non-reducing end, that is CBH I type activity binds strongly to all accessible regions of the cellulose and concomitantly has low hydrolytic activity. Depending on the enzyme concentration and conditions, such components can give up to 10% glucose as a secondary product with cellobiose being the primary product.

Accordingly, CBH I type components and CBH II type components refer to those fungal cellulase components which exhibit textile activity properties similar to CBH I and CBH II components of *Trichoderma longibrachiatum*, respectively. As noted above, for CBH I type components, this includes the property of enhancing strength loss of cotton-containing fabrics when used in a ratio with EG type components of between 5:1 to 1:5. In a preferred embodiment and when used in combination with EG type components, the CBH I type components of *Trichoderma longibrachiatum* can impart an incremental cleaning benefit. Additionally, it is contemplated that the CBH I components of *Trichoderma longibrachiatum*, when used alone or in combination with EG type components, can impart an incremental softening benefit.

"CBH II type cellulase components" refer to those components which exhibit exocellobiohydrolase activity similar to that of CBH II derived from *T. longibrachiatum*. Accordingly, the cellulase composition employed in the compositions of the present invention can contain CBH II type cellulase components in addition to CBH I type cellulase components and EG components. When so employed, the amount of CBH II type cellulase components is generally from about 0.001 to about 30 weight percent relative to the CBH I type cellulase component in the compositions. However, in the preferred embodiment, the cellulase composition contains no CBH II type cellulase components. In fact, our results indicate that CBH II, when employed at the same concentrations as CBH I, will not demonstrate the same cleaning benefits when combined with EG components that CBH I type cellulase components do. It is contemplated that CBH II may provide softening when combined with EG components.

Such exo-cellobiohydrolase type components may include components not traditionally classified as exo-cellobiohydrolases using activity tests such as those used to characterize CBH I and CBH II from *Trichoderma reesei*. For example, such components (a) are competitively inhibited by cellobiose ($K_i$ approximately 1 mM); (b) are unable to hydrolyze to any significant degree substituted celluloses, such as carboxymethylcellulose, etc.; and (c) hydrolyze phosphoric acid swollen cellulose and to a lesser degree highly crystalline cellulose. In contrast, it is believed that some fungal cellulase components which are characterized as CBH components by such activity tests, will impart improved feel, appearance, softening, color enhancement, and/or a stone washed appearance to cotton-containing fabrics with minimal strength loss when used alone in the cellulase composition. Accordingly, it is believed to be more accurate for the purposes herein to define such exo-cellobiohydrolases as EG type components because these components possess similar functional properties in textile uses as possessed by the endoglucanase components of *Trichoderma longibrachiatum*.

Fungal cellulase compositions enriched in CBH type components can be obtained by purification techniques. Specifically, the complete cellulase system can be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. After purification, the requisite amount of the desired components could be recombined.

Mixtures of cellulase components having the requisite ratio of CBH I type components to EG type cellulase components can be prepared by means other than isolation and recombination of the components. In this regard, it may be possible to modify the fermentation conditions for a natural microorganism in order to give relatively high ratios of CBH to EG components. However, in this regard, many attempts to modify the fermentation conditions for a natural microorganism in order to give relatively high ratios of CBH to EG components have failed, likely because CBH and EG components are coordinately regulated by the microorganism.

Likewise, recombinant techniques as set forth in the Examples can alter the relative ratio of CBH I type components to EG type components so as to produce a mixture of cellulase components having a relatively high ratio of CBH I type components to EG type components.

In regard to the above, a preferred method for the preparation of cellulase compositions enriched in CBH type components is by genetically modifying a microorganism so as to be incapable of producing one or more EG type components and/or overproducing CBH I type components preferably without producing any heterologous protein. In such a case, a requisite amount of the cellulase produced by such modified microorganism could be combined with the cellulase produced by the natural microorganism (i.e., containing EG type components) so as to provide for a cellulase composition containing CBH I type components and one or more EG type components wherein said cellulase composition has a protein weight ratio of CBH I type components to all EG type components of greater than 10:1.

In regard to the above, U.S. Ser. No. 07/770,049, filed Oct. 4, 1991, now abandoned which is a continuation-in-part of U.S. Ser. No. 07/593,919, filed Oct. 5, 1990, now abandoned both of which are incorporated herein by reference in its entirety, disclose methods for genetically engineering *Trichoderma longibrachiatum* so as to be incapable of producing one or more EG components and/or overproducing CBH I components. Moreover, the methods of that application create *Trichoderma reesei* strains which do not produce any heterologous proteins. U.S. Pat. No. 5,328,841 incorporated herein by reference disclose methods of producing a *T. longibrachiatum* EG I and EG II deleted strain. Likewise, Miller et al., "Direct and Indirect Gene Replacement in *Aspergillus nidulans*", *Molecular and Cellular Biology*, p. 1714–1721 (1985) disclose methods for deleting genes in *Aspergillus nidulans* by DNA mediated transformation using a linear fragment of homologous DNA.

In view of the above, the deletion of the genes responsible for producing EG I type, EG II and/or EG III type cellulase components would have the effect of enriching the amount of CBH I components present in the cellulase composition.

Additionally, a requisite amount of one or more EG type components purified by conventional procedures can be added to a cellulase composition produced from a microorganism genetically engineered so as to be incapable of producing EG type components so as to achieve a specified ratio of CBH I type components to EG type components, i.e., a cellulase composition free of all EG type components so as to be enriched in CBH I type components can be formulated to contain 1 weight percent of an EG type component merely by adding this amount of a purified EG type component to the cellulase composition.

"β-Glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose; such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and, thus, are often called aryl-glucosidases. It should be noted that not all aryl glucosidases are BG components, in that some do not hydrolyze cellobiose.

It is contemplated that the presence or absence of BG components in the cellulase composition can be used to regulate the activity of any CBH components in the composition. Specifically, because cellobiose is produced during cellulose degradation by CBH components, and because high concentrations of cellobiose are known to inhibit CBH activity, and further because such cellobiose is hydrolyzed to glucose by BG components, the absence of BG components in the cellulase composition will "turn-off" CBH activity when the concentration of cellobiose reaches inhibitory levels. It is also contemplated that one or more additives (e.g., cellobiose, glucose, etc.) can be added to the cellulase composition to effectively "turn-off", directly or indirectly, some or all of the CBH I type activity as well as other CBH activity. On the other hand, a cellulase composition containing added amounts of BG components may increase overall hydrolysis of cellulase if the level of cellobiose generated by the CBH components becomes restrictive of such overall hydrolysis in the absence of added BG components.

Methods to either increase or decrease the amount of BG components in the cellulase composition are disclosed in U.S. Ser. No. 07/807,028, filed Dec. 10, 1991, as Attorney Docket No. 010055-077 now abandoned and entitled "IMPROVED SACCHARIFICATION OF CELLULOSE BY CLONING AND AMPLIFICATION OF THE β-GLUCOSIDASE GENE OF *TRICHODERMA REESEI*", which is a continuation-in-part of U.S. Ser. No. 07/625,140, filed Dec. 10, 1990, now abandoned both of which are incorporated herein by reference in their entirety.

Fungal cellulases can contain more than one BG component. The different components generally have different isoelectric points which allow for their separation via ion exchange chromatography and the like. Either a single BG component or a combination of BG components can be employed.

When employed in textile treatment solutions, the BG component is generally added in an amount sufficient to prevent inhibition by cellobiose of any CBH and EG components, and particularly CBH I type cellulase components, by cellobiose. The amount of BG component added depends upon the amount of cellobiose produced in the textile composition which can be readily determined by the skilled artisan. However, when employed, the weight percent of BG component relative to any CBH type components present in the cellulase composition is preferably from about 0.2 to about 10 weight percent and more preferably, from about 0.5 to about 5 weight percent.

Preferred cellulases for use in preparing the cellulase compositions used in this invention are those obtained from *Trichoderma longibrachiatum, Trichoderma koningii*, Penicillium sp., *Humicola insolens*, and the like. Certain cellulases are commercially available, i.e., CELLUCAST cellulase (available from Novo Industry, Copenhagen, Denmark), RAPIDASE cellulase (available from Gist Brocades, N.V., Delft, Holland), CYTOLASE 123 cellulase (available from Genencor International, South San Francisco, Calif.) and the like. Other cellulases can be readily isolated by art recognized fermentation and isolation procedures.

The term "buffer" refers to art recognized acid/base reagents which stabilize the cellulase solution against undesired pH shifts during the cellulase treatment of the cotton-containing fabric. In this regard, it is art recognized that cellulase activity is pH dependent. That is to say that a specific cellulase composition will exhibit cellulolytic activity within a defined pH range with optimal cellulolytic activity generally being found within a small portion of this defined range. The specific pH range for cellulolytic activity will vary with each cellulase composition. As noted above, while many cellulases will exhibit cellulolytic activity within an acidic to neutral pH profile, there are some cellulase compositions which exhibit cellulolytic activity in an alkaline pH profile.

During cellulase treatment of the cotton-containing fabric, it is possible that the pH of the initial cellulase solution could be outside the range required for cellulase activity. It is further possible for the pH to change during treatment of the cotton-containing fabric, for example, by the generation of a reaction product which alters the pH of the solution. In either event, the pH of an unbuffered cellulase solution could be outside the range required for cellulolytic activity. When this occurs, undesired reduction or cessation of cellulolytic activity in the cellulase solution occurs. For example, if a cellulase having an acidic activity profile is employed in a neutral unbuffered aqueous solution, then the pH of the solution may result in lower cellulolytic activity. On the other hand, the use of a cellulase having a neutral or alkaline pH profile in a neutral unbuffered aqueous solution should initially provide significant cellulolytic activity.

In view of the above, the pH of the cellulase solution should be maintained within the range required for cellulolytic activity. One means of accomplishing this is by simply monitoring the pH of the system and adjusting the pH as required by the addition of either an acid or a base. However, in a preferred embodiment, the pH of the system is preferably maintained within the desired pH range by the use of a buffer in the cellulase solution. In general, a sufficient amount of buffer is employed so as to maintain the pH of the solution within the range wherein the employed cellulase exhibits activity. Insofar as different cellulase compositions have different pH ranges for exhibiting cellulase activity, the specific buffer employed is selected in relationship to the specific cellulase composition employed. The buffer(s) selected for use with the cellulase composition employed can be readily determined by the skilled artisan taking into account the pH range and optimum for the cellulase composition employed as well as the pH of the cellulase solution. Preferably, the buffer employed is one which is compatible with the cellulase composition and which will maintain the pH of the cellulase solution within the pH range required for optimal activity. Suitable buffers include sodium citrate, ammonium acetate, sodium acetate, disodium phosphate, and any other art recognized buffers.

"Degradation resistant" refers to the diminished capacity of a cellulase composition of this invention to degrade cotton fabric. In general, degradation of cotton fabric by a cellulase composition is measured by the degree of thinning, weakening and/or tearing produced in the cotton fabric.

Degradation is measured by testing the tensile strength of each garment/swatch. The tensile strength of cotton-containing fabrics can be measured in a warp and fill direction which are at right angles to each other.

Accordingly, the term "warp tensile strength" as used herein refers to the tensile strength of the cotton-containing fabric as measured along the length of the cotton-containing fabric whereas the term "fill tensile strength" refers to the tensile strength of the cotton-containing fabric as measured across the width of the cotton-containing fabric. The tensile strength of the resulting cotton-containing fabric treated with a cellulase solution is compared to its tensile strength prior to treatment with the cellulase solution so as to determine the strength reducing effect of the treatment. If the tensile strength is reduced too much, the resulting cotton-containing fabric will easily tear and/or form holes. Accordingly, it is desirable to maintain a tensile strength (both warp and fill) after treatment which is at least about 50% of the tensile strength before treatment.

The tensile strength of cotton-containing fabrics is readily conducted following ASTM D1682 test methodology. Equipment suitable for testing the tensile strength of such fabrics include a Scott tester or an Instron tester, both of which are commercially available. In testing the tensile strength of cotton-containing fabrics which have been treated with cellulase solutions, care should be taken to prevent fabric shrinkage after treatment and before testing. Such shrinkage would result in erroneous tensile strength data.

It is contemplated that the CBH II component, when employed at the same concentrations as CBH I, may provide softening. As a further embodiment of this invention, the CBH II component is substituted for the CBH I component, when softening is desired. In the event that CBH II is used in the invention, in place of or in addition to the CBH I component, to provide a softening effective amount, the ratio of CBH I and CBH II components to EG components is preferably 10:1 and more preferably 20:1.

2. Methodology

The present invention is directed to the discovery that beneficial properties heretofore imparted to cotton-containing fabrics by whole cellulase or by cellulase containing substantial amounts of EG type components can also be imparted to cotton-containing fabrics by cellulase compositions containing some EG components albeit at a ratio of CBH I type components to EG type components of greater than 10:1 to 400:1 and preferably from greater than 10:1 to about 100:1. At higher ratios of CBH I type components to EG type components the beneficial effects of these cellulase compositions become more evident with repeated treatments. In addition, to imparting the desired beneficial properties, the cellulase compositions described herein achieve such beneficial properties with reduced strength loss.

Enhancements to the cotton-containing fabric are achieved by those methods heretofore used and illustrated in Example 2 hereinbelow. For example, cotton-containing fabrics having improved feel can be achieved as per Japanese Patent Application Nos. 58-36217 and 58-54032, as well as Ohishi et al., "Reformation of Cotton-Fabric by Cellulase" and *JTN* December 1988 journal article "What's New—Weight Loss Treatment to Soften the Touch of Cotton Fabric". The teachings of each of these references is incorporated herein by reference.

Similarly, methods for improving both the feel and appearance of cotton-containing fabrics include contacting the fabric with an aqueous solution containing cellulase under conditions so that the solution is agitated and so that a cascading effect of the cellulase solution over the cotton-containing fabric is achieved. Such methods result in improved feel and appearance of the so treated cotton-containing fabric and are described in U.S. Pat. No. 5,232,851 and which is incorporated herein by reference in its entirety.

Methods for the enhancement of cotton-containing knits are described in International Textile Bulletin, Dyeing/Printing/Finishing, pages 5 et seq., $2^{nd}$ Quarter, 1990, which is incorporated herein by reference.

Likewise, methods for imparting a stone washed appearance to cotton-containing denims are described in U.S. Pat. No. 4,832,864, which is incorporated herein by reference in its entirety.

Other methods for enhancing cotton-containing fabrics by treatment with a cellulase composition are known in the art. Preferably, in such methods, the treatment of the cotton-containing fabric with cellulase is conducted prior to finishing the cotton-containing fabric.

As noted above, the present invention is an improvement over prior art methods for treating cotton-containing fabrics insofar as the present invention employs a specific cellulase composition which minimizes strength loss in the treated fabric. The cellulase composition employed herein is a fungal cellulase composition which comprises a CBH I type components and EG type components wherein the cellulase composition has a weight ratio of CBH I type components to all EG type components of greater than 10:1.

Additionally, the use of the cellulase compositions described herein also result in fabric/color enhancement of stressed cotton-containing fabrics. Specifically, during the manufacture of cotton-containing fabrics, the fabric can become stressed and when so stressed, it will contain broken and disordered fibers. Such fibers detrimentally impart a worn and dull appearance to the fabric. However, when treated in the method of this invention, the so stressed fabric is subject to fabric/color enhancement. This is believed to arise by removal of some of the broken and disordered fibers which has the effect of restoring the appearance of the fabric prior to becoming stressed.

Additionally, it is contemplated that by employing the cellulase composition described herein, wherein the EG type component is a EG III type component, with pigment type dyed fabrics (e.g., denims), these cellulase compositions may cause less redeposition of dye.

The cellulase compositions described above are employed in an aqueous solution which contains cellulase and other optional ingredients including, for example, a buffer, a surfactant, a scouring agent, and the like. The concentration of the cellulase composition employed in this solution is generally a concentration sufficient for its intended purpose. That is to say that an amount of the cellulase composition is employed to provide the desired enhancement(s) to the cotton-containing fabric. The amount of the cellulase composition employed is also dependent on the equipment employed, the process parameters employed (the temperature of the cellulase solution, the exposure time to the cellulase solution, and the like), the cellulase activity (e.g., a cellulase solution will require a lower concentration of a more active cellulase composition as compared to a less active cellulase composition), and the like. The exact concentration of the cellulase composition can be readily determined by the skilled artisan based on the above factors as well as the desired effect. Preferably, the concentration of the cellulase composition in the cellulase solution employed herein is from about 0.01 gram/liter of cellulase solution to about 50.0 grams/liter of cellulase solution; and more preferably, from about 0.05 grams/liter of cellulase solution to about 10.0 gram/liter of cellulase solution. (The cellulase concentration recited above refers to the weight of total protein).

When a buffer is employed in the cellulase solution, the concentration of buffer in the aqueous cellulase solution is that which is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the cellulase solution within the pH range required for optimal cellulase activity. In general, buffer concentration in the cellulase solution is about 0.005N and greater. Preferably, the concentration of the buffer in the cellulase solution is from about 0.01 to about 0.5N, and more preferably, from about 0.05 to about 0.15N. It is possible that increased buffer concentrations in the cellulase solution may enhance the rate of tensile strength loss of the treated fabric.

In addition to cellulase and a buffer, the cellulase solution can optionally contain a small amount of a surfactant in order to improve wettability. The amount of surfactant used is generally less than about 2 weight percent, and preferably from about 0.01 to about 2 weight percent; but in any event, is less than a cleaning effective amount. Suitable surfactants include any .surfactant compatible with the cellulase and the fabric including, for example, anionic, non-ionic and ampholytic surfactants.

Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Mixtures of surfactants can also be employed.

The liquor ratios, i.e., the ratio of weight of cellulase solution to the weight of fabric, employed herein is generally an amount sufficient to achieve the desired enhancement in the cotton-containing fabric and is dependent upon the process used and the enhancement to be achieved. Preferably, the liquor ratios are generally from about 0.1:1 and greater, and more preferably greater than about 1:1 and even more preferably greater than about 10:1. Use of liquor ratios of greater than about 50:1 are usually not preferred from an economic viewpoint.

Reaction temperatures for cellulase treatment are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 30° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase. As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 50° C.

Reaction times are generally from about 0.1 hours to about 24 hours and, preferably, from about 0.25 hours to about 5 hours.

The cotton-containing fabrics treated in the methods described above using such cellulase compositions possess reduced strength loss as compared to the same cotton-containing fabric treated in the same manner with a complete cellulase composition.

In a preferred embodiment, a concentrate can be prepared for use in the methods described herein. Such concentrates would contain concentrated amounts of the cellulase composition described above, buffer and surfactant, preferably in an aqueous solution. When so formulated, the concentrate can readily be diluted with water so as to quickly and accurately prepare cellulase solutions having the requisite concentration of these additives. Preferably, such concentrates will comprise from about 0.1 to about 50 weight percent of a cellulase composition described above (protein); from about 10 to about 50 weight percent buffer; from about 10 to about 50 weight percent surfactant; and from about 0 to about 80 weight percent water. When aqueous concentrates are formulated, these concentrates can be diluted by factors of from about 2 to about 200 so as to arrive at the requisite concentration of the components in the cellulase solution. As is readily apparent, such concentrates will permit facile formulation of the cellulase solutions as well as permit feasible transportation of the concentration to the location where it will be used. The cellulase composition as described above can be added to the concentrate either in a liquid diluent, in granules, in emulsions, in gels, in pastes, and the like. Such forms are well known to the skilled artisan.

When a solid cellulase concentrate is employed, the cellulase composition is generally a granule, a powder, an agglomerate and the like. When granules are used, the granules are preferably formulated so as to contain a cellulase protecting agent. See, for instance, U.S. Ser. No. 07/642,669, filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES", now abandoned which application is incorporated herein by reference in its entirety. Likewise, the granules can be formulated so as to contain materials to reduce the rate of dissolution of the granules into the wash medium. Such materials and granules are disclosed in U.S. Ser. No. 07/642,596, filed on Jan. 17, 1991, as Attorney Docket No. GCS171-US1 U.S. Pat. No. 5,254,283 and entitled "GRANULAR COMPOSITIONS", which application is incorporated herein by reference in its entirety.

It is contemplated that the cellulase compositions described herein can additionally be used in a pre-wash and as a pre-soak either as a liquid or a spray. It is still further contemplated that the cellulase compositions described herein can also be used in home use as a stand alone composition suitable for enhancing color and appearance of fabrics. See, for example, U.S. Pat. No. 4,738,682, which is incorporated herein by reference in its entirety.

The following examples are offered to illustrate the present invention and should not be construed in any way as limiting its scope.

EXAMPLES

Example 1

Fractionation of Cellulase Components

CYTOLASE 123 cellulase, a commercially available cellulase system (from Genencor International, Inc., South San Francisco, Calif.) derived from wild type *Trichoderma longibrachiatum*, was fractionated. The normal distribution of cellulase components in this cellulase system is as follows:

| | |
|---|---|
| CBH I | 45–55 weight percent |
| CBH II | 13–15 weight percent |
| EG I | 11–13 weight percent |
| EG II | 8–10 weight percent |
| EG III | Less than 4 weight percent |
| BG | 0.5–1 weight percent |

The fractionation was done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin equilibrated with 10 mM sodium phosphate buffer pH=6.8. The fraction bound on this column contained CBH I and EG I. These components were separated by gradient elution using an aqueous gradient containing from 0 to about 500 mM sodium chloride. The fraction not bound on this column contained CBH II, EG II and EG III. These fractions were desalted using a column of Sephadex G-25 gel filtration resin equilibrated with 10 mM sodium citrate, pH 4.5. This solution, 200 ml, was then loaded onto a column of 20 ml of SP Trisacryl M cation exchange resin. CBH II, EG II, and EG III were eluted separately using an aqueous gradient containing from 0 to about 200 mM sodium chloride.

Following procedures similar to that of Example 1 above, other cellulase systems which can be separated into their components include CELLUCAST (available from Novo Industry, Copenhagen, Denmark), RAPIDASE (available from Gist Brocades, N.V., Delft, Holland), and cellulase systems derived from *T. koningii*, Penicillium sp. and the like.

Example 2

Softness Assay of Cellulase Compositions

The purpose of this example is to determine the softness effect of the cellulase composition in the absence of a surfactant.

Certain cellulase compositions produced by genetically modifying the *T. longibrachiatum* microorganism so as to be incapable of producing one or more EG-type components which methods do not produce any heterologous protein. The method to produce the cellulase compositions is described in the Examples hereinbelow. These combinations will be employed in the swatch washing procedure set forth below. This procedure tests the ability of different cellulase compositions to soften cotton swatches. In this procedure, the degree of softness is measured by whole fabric feel by a group of panelists.

The washing machine (Unimac 50 lb. capacity, rotary drum) is filled with 9.5 gallons of cold water. The buffer (42 grams of citric acid anhydrous and 101 grams of sodium phosphate dibasic) are added to the washing machine. The temperature of the wash liquor is adjusted to 40° C. and the test cellulase composition added. If required, the pH is adjusted to pH 5.0 by adding citric acid or sodium phosphate. Three 100% cotton terry towels, 25"×46", are washed for 45 minutes at 37 rpm at 60°–80° C. and then extracted for 2 minutes at a maximum rpm of 460. The towels are rinsed in 24 gallons of water at 34° C. for 5 minutes. The towels are again extracted for 2 minutes at a maximum rpm of 460. The towels are dried in .a conventional drier for 50 minutes on the high temperature setting of approximately 60°–80° C.

After washing, the towels are then labeled (to prevent panelists from ascertaining how the fabric had been treated) and tested for softness by a group of panelists by whole fabric feel and by mechanized test methods. The panelists evaluate the fabrics by a preference for "softer" and "rougher" fabric.

The first set of fabrics analyzed is treated with an EG I and EG II deleted cellulase composition prepared from *Trichoderma longibrachiatum* genetically modified in a manner similar to that described below, so as to be incapable of expressing EG I and EG II. Insofar as EG I and EG II comprises up to about 23 percent of the cellulase composition, deletion of this component results in enriched levels of all of the CBH components. Moreover, because EG components, other than EG I and II, comprise about 5 weight percent of this composition, the CBR I to EG ratio is about 12:1.

The second set of fabrics analyzed are tested with a control solution which does not contain a cellulase composition.

It is contemplated that cotton fabric treated with the EG I/II deleted cellulase composition will have increased softness when compared to cotton fabric treated with the control solution which does not contain a cellulase composition. The EG I/II deleted cellulase composition comprises a cellulase composition containing CBH I and EG components wherein the weight ratio of CBH I to EG components is at least 10:1. This anticipated result is suggested by the discovery that a cellulase composition comprising CBH I and EG components where the protein weight ratio of CBH I components to EG components is at least 10:1 in the presence of surfactant will impart softening to cotton containing fabric. See, U.S. Ser. No. 07/876,927.

Example 3

Selection for pyr4⁻ Derivatives of *Trichoderma longibrachiatum*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and, thus, poisons the cells. However, cells defective in the pyr4 gene are resistant to this inhibitor but require uridine for growth. It is, therefore, possible to select for pyr4 derivative strains using FOA. In practice, spores of *T. longibrachiatum* strain RL-P37 (Sheir-Neiss, G. and Montenecourt, B. S., *Appl.*

*Microbiol. Biotechnol.*, 20, p. 46–53 (1984)) were spread on the surface of a solidified medium containing 2 mg/ml uridine and 1.2 mg/ml FOA. Spontaneous FOA-resistant colonies appeared within three to four days and it was possible to subsequently identify those FOA-resistant derivatives which required uridine for growth. In order to identify those derivatives which specifically had a defective pyr4 gene, protoplasts were generated and transformed with a plasmid containing a wild-type pyr4 gene (see Examples 5 and 6). Following transformation, protoplasts were plated on medium lacking uridine. Subsequent growth of transformed colonies demonstrated complementation of a defective pyr4 gene by the plasmid-borne pyr4 gene. In this way, strain GC69 was identified as a pyr4⁻ derivative of strain RL-P37.

Example 4

Preparation of CBH I Deletion Vector

A cbh1 gene encoding the CBH I protein was cloned from the genomic DNA of *T. longibrachiatum* strain RL-P37 by hybridization with an oligonucleotide probe designed on the basis of the published sequence for this gene using known probe synthesis methods (Shoemaker et al., 1983b). The cbh1 gene resides on a 6.5 kb PstI fragment and was inserted into PstI cut pUC4K (purchased from Pharmacia Inc., Piscataway, N.J.) replacing the Kan' gene of this vector using techniques known in the art, which techniques are set forth in Maniatis et al. (1989) and incorporated herein by reference. The resulting plasmid, pUC4K::cbh1 was then cut with HindIII and the larger fragment of about 6 kb was isolated and relegated to give pUC4K::cbh1ΔH/H (see FIG. 1). This procedure removes the entire cbh1 coding sequence and approximately 1.2 kb upstream and 1.5 kb downstream of flanking sequences. Approximately, 1 kb of flanking DNA from either end of the original PstI fragment remains.

The *T. longibrachiatum* pyr4 gene was cloned as a 6.5 kb HindIII fragment of genomic DNA in pUC18 to form pTpyr2 (Smith et al., 1991) following the methods of Maniatis et al., supra. The plasmid pUC4K::cbh1ΔH/H was cut with HindIII and the ends were dephosphorylated with calf intestinal alkaline phosphatase. This end dephosphorylated DNA was ligated with the 6.5 kb HindIII fragment containing the *T. longibrachiatum* pyr4 gene to give pΔCBHIpyr4. FIG. 1 illustrates the construction of this plasmid.

Example 5

Isolation of Protoplasts

Mycelium was obtained by inoculating 100 ml of YEG (0.5% yeast extract, 2% glucose) in a 500 ml flask with about $5 \times 10^7$ *T. longibrachiatum* GC69 spores (the pyr4⁻ derivative strain). The flask was then incubated at 37° C. with shaking for about 16 hours. The mycelium was harvested by centrifugation at 2,750× g. The harvested mycelium was further washed in a 1.2M sorbitol solution and resuspended in 40 ml of a solution containing 5 mg/ml Novozym$^R$ 234 solution (which is the trade name for a multicomponent enzyme system containing 1,3-alpha-glucanase, 1,3-beta-glucanase, laminarinase, xylanase, chitinase and protease from Novo Biolabs, Danbury, Conn.); 5 mg/ml MgSO$_4$.7H$_2$O; 0.5 mg/ml bovine serum albumin; 1.2M sorbitol. The protoplasts were removed from the cellular debris by filtration through Miracloth (Calbiochem Corp, La Jolla, Calif.) and collected by centrifugation at 2,000× g. The protoplasts were washed three times in 1.2M sorbitol and once in 1.2M sorbitol, 50 mM CaCl$_2$, centrifuged and resuspended at a density of approximately $2 \times 10^8$ protoplasts per ml of 1.2M sorbitol, 50 mM CaCl$_2$.

Example 6

Transformation of Fungal Protoplasts with pΔCBHIpyr4

200 µl of the protoplast suspension prepared in Example 5 was added to 20 µl of EcoRI digested pΔCBHIpyr4 (prepared in Example 4) in TE buffer (10 mM Tris, pH 7.4; 1 mM EDTA) and 50 µl of a polyethylene glycol (PEG) solution containing 25% PEG 4000, 0.6M KCl and 50 mM CaCl$_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2M sorbitol and 50 mM CaCl$_2$ was added thereto and this solution was further mixed. The protoplast solution was then immediately added to molten aliquots of Vogel's Medium N (3 grams sodium citrate, 5 grams KH$_2$PO$_4$, 2 grams NH$_4$NO$_3$, 0.2 grams MgSO$_4$.7H$_2$O, 0.1 gram CaCl$_2$.2H$_2$O, 5 µg α-biotin, 5 mg citric acid, 5 mg ZnSO$_4$.7H$_2$O, 1 mg Fe(NH$_4$)$_2$.6H$_2$O, 0.25 mg CuSO$_4$.5H$_2$O, 50 µg MnSO4.4H$_2$O per liter) containing an additional 1% glucose, 1.2M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene insert in pΔCBHIpyr4. These colonies were subsequently transferred and purified on a solid Vogel's medium N containing as an additive, 1% glucose and stable transformants were chosen for further analysis.

At this stage stable transformants were distinguished from unstable transformants by their faster growth rate and formation of circular colonies with a smooth, rather than ragged outline on solid culture medium lacking uridine. In some cases a further test of stability was made by growing the transformants on solid non-selective medium (i.e. containing uridine), harvesting spores from this medium and determining the percentage of these spores which will subsequently germinate and grow on selective medium lacking uridine.

Example 7

Construction of pΔEGIpyr-3 and Transformation of a pyr4 Deficient Strain of *T. longibrachiatum*

The *T. longibrachiatum* egl1 gene, which encodes EG I has been cloned as a 4.2 kb HindIII fragment of genomic DNA from strain RL-P37 by hybridization with oligonucleotides synthesized according to the published sequence (Pentilia et al., 1986, *Gene*, 45: 253–263; van Arsdell et al., 1987, *Bio/Technology*, 5: 60–64).

This DNA fragment was inserted at the HindIII site of pUC100. An internal 1 kb EcoRV fragment which extended from a position close to the middle of the EG I coding sequence to a position beyond the 3' end of the coding sequence was removed by enzyme digestion and was replaced by ligation with a 2.2 kb BamHI—HindIII fragment containing the cloned *A. niger* pyrG gene (Wilson et al., 1988, *Nucl. Acids Res.*, 16, p. 2339) to give pΔEGIpyrG-3 (FIG. 2). Transformation of a pyr4 deficient strain of *T. longibrachiatum* (strain GC69) by the method set forth in Examples 5 and 6, with pΔEGIpyr-3, after it had been digested with HindIII to release the fragment containing the pyrG gene with flanking regions from the egl1 locus at either end, led to transformants in which the genomic egl1 gene was disrupted by a mechanism outlined in FIG. 3. DNA was extracted from transformants, digested with HindIII, subjected to agarose gel electrophoresis and blotted onto a membrane filter. The filter was hybridized with radiolabelled pΔEGIpyr-3. In the untransformed strain of *T. longibrachiatum* the egl1 gene was present on a 4.2 kb HindIII fragment of DNA. However, following deletion of the egl1 gene by integration of the desired fragment from pΔEGIpyr-3 this 4.2 kb HindIII fragment disappeared and was replaced by a HindIII fragment approximately 1.2 kb larger in size. This pattern was observed for one transformant which was designated ΔEGI-3.

Example 8

Construction of PAΔEGII-1 and Deletion of the EG II Gene

The egl3 gene, encoding EG II (also referred to in the literature as EG III), was cloned from *T. longibrachiatum* strain RE-P37 as a 4 kb PstI genomic DNA fragment by hybridization with oligonucleotides synthesized according to the published sequence (Saloheimo et al., 1988, *Gene*, 63: 11–21). This DNA fragment was inserted into the PstI site of pUC18. This plasmid, pEGII, was subsequently digested with EcoRV to remove the entire EG II coding region on an approximately 2 kb segment extending from a position approximately 180 bp 5' of the EGII coding region to a position a few hundred base pairs beyond the end of the coding region. This segment was replaced with an SspI fragment of *Aspergillus nidulans* genomic DNA containing the amdS gene (Corrick et al., 1987, *Gene*, 53: 63–71) to create plasmid PAΔEGII-1 (See FIG. 4).

Wild-type strains of *T. longibrachiatum* are unable to grow on acetamide as a sole nitrogen source. Transformation with the amdS gene confers this ability and this is the basis for the selection system for transformants containing this gene.

Protoplasts of strain ΔEGI-3 were transformed, by the methods described in Examples 5 and 6, with pAΔEGII-1 which had been digested with HindIII and EcoRI and transformants able to grow on acetamide were selected. Subsequently, DNA was extracted from stable transformants, digested with PstI, subjected to agarose gel electrophoresis and blotted onto a membrane filter. The filter was hybridized with radiolabelled pAΔEGII-1. -Homologous integration of the HindIII-EcoRI fragment from pAΔEGII-1, which contained egl3 flanking regions and amdS, at the genomic egl3 locus in a transformant lead to the 4 kb genomic PstI fragment containing the egl3 gene being replaced by smaller PstI fragments including two which would be approximately 1.0 and 2.8 kb in length. This pattern of hybridization was observed for one transformant which was designated strain AAEG-1. This strain has deletions in both the EGI and EGII encoding genes and consequently is unable to produce either of these proteins.

The methods described in Examples 3 to 8 and in U.S. Ser. No. 07/770,049, filed Oct. 4, 1991 (incorporated herein by reference in its entirety) now abandoned may be used to obtain *T. longibrachiatum* transformants which are unable to produce any or all of the following cellulase components; EG I, EG II, EG III and CBH II components. It is noted that Examples 3–6 herein are identical with Examples 1–4 of U.S. Ser. No. 07/770,049. For the sake of completion, the procedures set forth in Examples 5–9 of U.S. Ser. No. 07/770,049 are repeated below as Examples 9–13:

Example 9

Analysis of the Transformants

DNA was isolated from the transformants obtained in Example 6 after they were grown in liquid Vogel's medium N containing 1% glucose. These transformant DNA samples were further cut with a PstI restriction enzyme and subjected to agarose gel electrophoresis. The gel was then blotted onto a Nytran membrane filter and hybridized with a $^{32}$P labelled pΔCBHIpyr4 probe. The probe was selected to identify the native cbh1 gene as a 6.5 kb PstI fragment, the native pyr4 gene and any DNA sequences derived from the transforming DNA fragment.

The radioactive bands from the hybridization were visualized by autoradiography. The autoradiograph is seen in FIG. 5. Five samples were run as described above, hence samples A, B, C, D, and E. Lane E is the untransformed strain GC69 and was used as a control in the present analysis. Lanes A–D represent transformants obtained by the methods described above. The numbers on the side of the autoradiograph represent the sizes of molecular weight markers. As can be seen from this autoradiograph, lane D does not contain the 6.5 kb CBHI band, indicating that this gene has been totally deleted in the transformant by integration of the DNA fragment at the cbh1 gene. The cbh1 deleted strain is called P37PΔCBHI. FIG. 6 outlines the deletion of the *T. longibrachiatum* cbh1 gene by integration through a double cross-over event of the larger EcoRI fragment from pΔCBHIpyr4 at the cbh1 locus on one of the *T. longibrachiatum* chromosomes. The other transformants analyzed appear identical to the untransformed control strain.

Example 10

Analysis of the Transformants with pIntCBHI

The same procedure was used in this example as in Example 9, except that the probe used was changed to a $^{32}$P labelled pIntCBHI probe. This probe is a pUC-type plasmid containing a 2 kb BglII fragment from the cbh1 locus within the region that was deleted in pUC4K::cbh1ΔH/H. Two samples were run in this example including a control, sample A, which is the untransformed strain GC69 and the transformant P37PΔCBHI, sample B. As can be seen in FIG. 7, sample A contained the cbh1 gene, as indicated by the band at 6.5 kb; however the transformant, sample B, does not contain this 6.5 kb band and therefore does not contain the cbh1 gene and does not contain any sequences derived from the pUC plasmid.

Example 11

Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4.5H_2O$, 0.001% $FeSO_4.7H_2O$, 0.000128% $ZnSO_4.7H_2O$, 0.0000054% $Na_2MoO_4.2H_2O$, 0.0000007% $MnCl.4H_2O$). The medium was incubated with shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. with shaking. The supernatant was then collected from these cultures and the mycelium was discarded. Samples of the culture supernatant were analyzed by isoelectric focusing using a Pharmacia Phastgel system and pH 3–9 precast gels according to the manufacturer's instructions. The gel was stained with silver stain to visualize the protein bands. The band corresponding to the cbh1 protein was absent from the sample derived from the strain P37PΔCBHI, as shown in FIG. 8. This isoelectric focusing gel shows various proteins in different supernatant cultures of *T. longibrachiatum*. Lane A is partially purified CBHI; Lane B is the supernatant from an untransformed *T. longibrachiatum* culture; Lane C is the supernatant from strain P37PΔCBHI produced according to the methods of the present invention. The position of various cellulase components are labelled CBHI, CBHII, EGI, EGII, and EGIII. Since CBHI constitutes 50% of the total extracellular protein, it is the major secreted protein and hence is the darkest band on the gel. This isoelectric focusing gel clearly shows depletion of the CBHI protein in the P37PΔCBHI strain.

Example 12

Preparation of pPΔCBHII

Figure 9B:
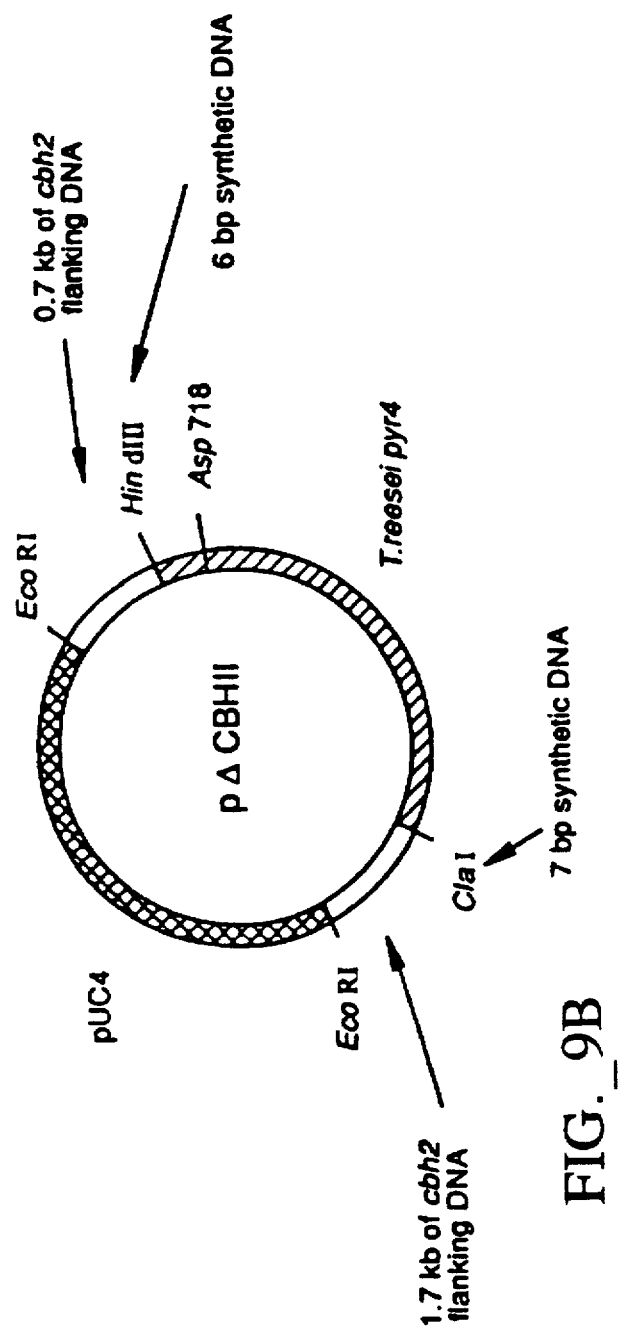
FIG. 9B is a representation of the cbh2 gene deletion vector pPΔCBHII.

The cbh2 gene of *T. longibrachiatum*, encoding the CBHII protein, has been cloned as a 4.1 kb EcoRI fragment of genomic DNA which is shown diagramatically in FIG. 9A (Chen et al., 1987, *Biotechnology*, 5: 274–278). This 4.1 kb fragment was inserted between the EcoRI sites of pUC4XL. The latter plasmid is a pUC derivative (constructed by R. M. Berka, Genencor International Inc.) which contains a multiple cloning site with a symetrical pattern of restriction endonuclease sites arranged in the order shown here: EcoRI, BamHI, SacI, SmaI, HindIII, XhoI, BglII, ClaI, BglII, XhoI, HindIII, SmaI, SacI, BamHI, EcoRI. Using methods known in the art, a plasmid, pPΔCBHII (FIG. 9B), has been constructed in which a 1.7 kb central region of this gene between a HindIII site (at 74 bp 3' of the CBHII translation initiation site) and a ClaI site (at 265 bp 3' of the last codon of CBHII) has been removed and replaced by a 1.6 kb HindIII-ClaI DNA fragment containing the *T. longibrachiatum* pyr4 gene.

The *T. longibrachiatum* pyr4 gene was excised from pTpyr2 (see Example 4) on a 1.6 kb NheI-SphI fragment and inserted between the SphI and XbaI sites of pUC219 (derived from pUC 119 [described in Wilson, et al., 1989, Gene, 77: 69–77] by expanding the multiple cloning site to include restriction sites for BglII, ClaI, and XhoI) to create p219M (Smith et al., 1991, *Curr. Genet* 19 p. 27–33). The pyr4 gene was then removed as a HindIII-ClaI fragment having seven bp of DNA at one end and six bp of DNA at the other end derived from the pUC219 multiple cloning site and inserted into the HindIII and ClaI sites of the cbh2 gene to form the plasmid pPΔCBHII (see FIG. 9B).

Digestion of this plasmid with EcoRI will liberate a fragment having 0.7 kb of flanking DNA from the cbh2 locus at one end, 1.7 kb of flanking DNA from the cbh2 locus at the other end and the *T. longibrachiatum* pyr4 gene in the middle.

Example 13

Deletion of the cbh2 gene in *T. longibrachiatum* strain GC69

Protoplasts of strain GC69 will be generated and transformed with EcoRI digested pPΔCBHII according to the methods outlined in Examples 5 and 6. DNA from the transformants will be digested with EcoRI and Asp718, and subjected to agarose gel electrophoresis. The DNA from the gel will be blotted to a membrane filter and hybridized with $^{32}$P labelled pPΔCBHII. Transformants will be identified which have a single copy of the EcoRI fragment from pPΔCBHII integrated precisely at the cbh2 locus. The transformants will also be grown in shaker flasks as in Example 11 and the protein in the culture supernatants examined by isoelectric focusing. In this manner *T. longibrachiatum* GC69 transformants which do not produce the CBHII protein will be generated.

While the invention has been described in terms of various preferred embodiments, the skilled artisan will appreciate that various modifications, substitutions, omissions, and changes may be made without departing from the spirit and scope thereof. Accordingly, it is intended that the scope of the present invention be limited solely by the scope of the following claims, including equivalents thereof.

What is claimed is:

1. In a method for enhancing the feel, appearance, for softening or for imparting color enhancement and/or a stoned-washed appearance to cotton-containing fabrics by treatment of the fabric with a composition comprising a naturally complete fungal cellulase composition which comprises CBH I type components and EG type components under conditions wherein the cellulase composition enhances the feel, appearance, for softening of the fabric or for imparting color enhancement and/or a stoned-washed appearance to the fabric wherein said improvement comprises modifying the fungal cellulase composition to comprise a protein weight ratio of CBH I type cellulase components to EG type components found in the modified cellulase composition to a ratio of from 10:1 to 400:1.

2. The method according to claim 1 wherein said cellulase composition is substantially free of CBH II type cellulase components.

3. The method according to claim 2 wherein said protein weight ratio of all CBH I type component to all EG type components is from greater than 20:1 to 400:1.

4. The method according to claim 3 wherein said protein weight ratio of CBH I type cellulase components to EG type components is from about 40:1 to 400:1.

5. The method according to claim 4, wherein said CBH I type cellulase comprises CBH I from Trichoderma.

6. The method according to claim 5, wherein Trichoderma comprises *Trichoderma reesei*.

7. The method according to claim 1, wherein said CBH I type cellulase comprises CBH I from Trichoderma.

8. The method according to claim 7, wherein Trichoderma comprises *Trichoderma reesei*.

9. In a method for enhancing the feel, appearance for softening or imparting imparting color enhancement or for imparting a stoned-washed appearance to cotton-containing fabrics by treatment of the fabric with an aqueous cellulase solution comprising a naturally complete fungal cellulase composition which comprises CBH I type components and EG type components wherein said method is conducted with agitation of the cellulase solution under conditions so as to produce a cascading effect of the cellulase solution over the fabric under conditions wherein the cellulase composition enhances the feel, appearance, and/or softening of the fabric and/or imparts color enhancement and/or a stoned-washed appearance to the fabric wherein the improvement comprises modifying the fungal cellulase composition to comprise a protein weight ratio of CBH I type cellulase components to all EG components found in the modified cellulase composition to a ratio of from 10:1 to 400:1.

10. A method according to claim 9 wherein said cellulase composition has a protein weight ratio of CBH I type components to all EG type components of from 20:1 to 400:1.

11. A method according to claim 9 wherein said cellulase composition has a protein weight ratio of CBH I type components to all EG type components of from 40:1 to 400:1.

* * * * *